US006331266B1

(12) United States Patent
Powell et al.

(10) Patent No.: US 6,331,266 B1
(45) Date of Patent: Dec. 18, 2001

(54) PROCESS OF MAKING A MOLDED DEVICE

(75) Inventors: Kenneth G. Powell; Larry A. Monahan, both of Raleigh, NC (US); Burton H. Sage, Jr., Vista, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/408,450

(22) Filed: Sep. 29, 1999

(51) Int. Cl.$^7$ .......................... B29C 33/42; B29C 33/44; B29C 43/10; B29C 45/26
(52) U.S. Cl. ......................... 264/313; 264/320; 264/322; 264/328.1; 264/337; 264/338
(58) Field of Search .................................... 264/219, 313, 264/320, 322, 328.1, 328.16, 337, 338

(56) References Cited

U.S. PATENT DOCUMENTS

| | | |
|---|---|---|
| 4,614,630 * | 9/1986 | Pluim, Jr. .............................. 264/219 |
| 5,250,023 | 10/1993 | Lee et al. . |
| 5,304,487 | 4/1994 | Wilding . |
| 5,498,392 | 3/1996 | Wilding . |
| 5,879,326 | 3/1999 | Godshall et al. . |
| 5,885,470 | 3/1999 | Parce . |

FOREIGN PATENT DOCUMENTS

| | | |
|---|---|---|
| 4307869A1 | 9/1994 | (DE) . |
| 437345A2 | 1/1991 | (EP) . |
| WO 97/48440 | 12/1997 | (WO) . |
| WO 00/74764A1 | 12/2000 | (WO) . |

OTHER PUBLICATIONS

IBM Technical Disclosure Bulletin, vol. 30 No. 5 Oct. 1987 (pp. 306–311).

* cited by examiner

Primary Examiner—Leo B. Tentoni
(74) Attorney, Agent, or Firm—Allen W. Wark, Esq.

(57) ABSTRACT

A device, preferably a micro-device, is molded from a plastic material by injection molding, compression molding or embossing. A microabrader can be molded having microneedles for abrading the stratum corneum of the skin to form an abraded site in the tissue for enhancing drug delivery. The micro-device is molded using a mold assembly having a silicon molding surface. The silicon molding surface can include a recess corresponding to the desired shape and length of the microneedles. The silicon molding surface enables micron and submicron size features to be molded from polymeric materials without the polymeric material adhering to the mold surface. Micro-devices having molded features having micron and submicron dimensions can be rapidly produced without the use of a release agent.

24 Claims, 6 Drawing Sheets

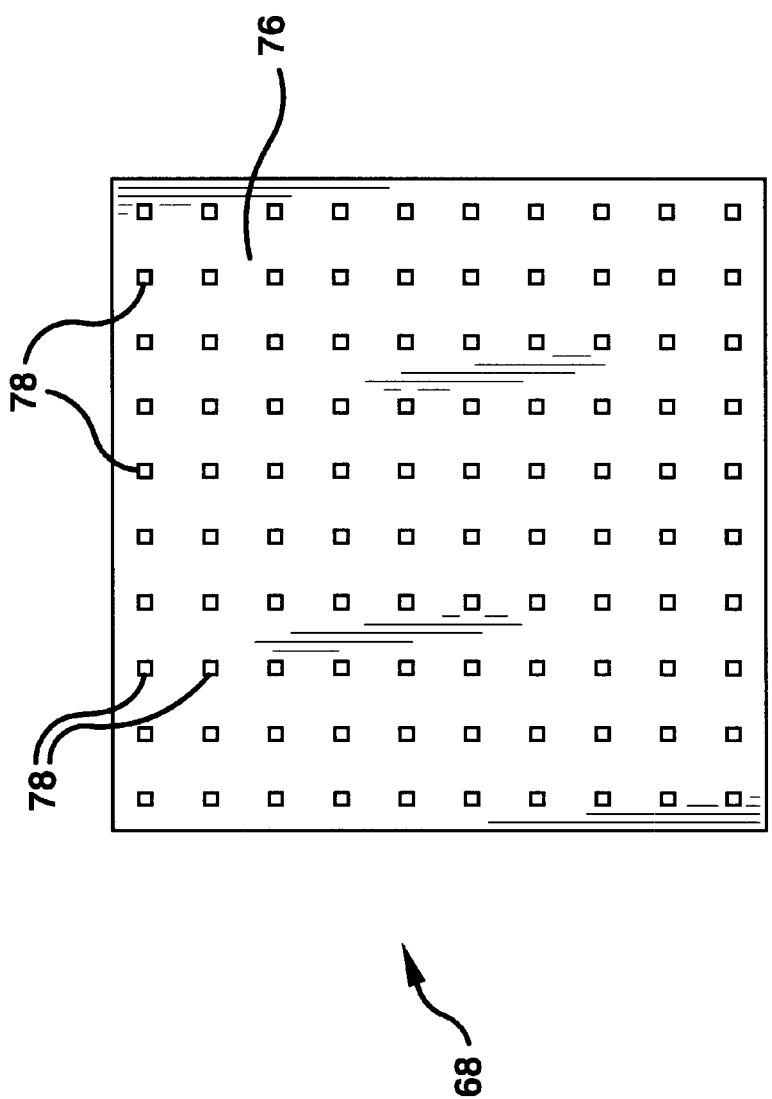

PROCESS OF MAKING A MOLDED DEVICE

FIELD OF THE INVENTION

The present invention relates to a method of manufacturing a device, and particularly, a micro-device. More particularly, the invention is directed to a method of molding a micro-device for medical use.

BACKGROUND OF THE INVENTION

There has been an increase in interest in processes for the manufacture of small devices in the field of biological and biochemical analysis. The manufacture of devices used for analytical testing uses techniques similar to those used in the electronics industry. Examples of these manufacturing techniques include photolithography and wet chemical etching. The devices are often made from solid substrates such as silicon and glass.

Microanalytical devices have been used for performing various analytical reactions. For example, U.S. Pat. No. 5,498,392 to Wilding et al. discloses a mesoscale device having microfabricated fluid channels and chambers in a solid substrate for the performance of nucleic acid amplification reactions. U.S. Pat. No. 5,304,487 to Wilding et al. discloses a mesoscale device having a cell handling region for detecting an analyte in a sample. The microchannels and chambers have a cross-sectional dimension ranging from 0.1 micron to 500 microns. U.S. Pat. No. 5,885,470 to Parce et al. discloses a microfluidic transport device made from a polymeric substrate having fluid channels that can be a few microns wide.

The prior processes for microfabrication of polymeric substrates typically involve stamp molding or embossing. These processes often require the use of a release agent or coating on the molding surface.

There has also been an increased interest in microneedle injection for the transdermal delivery of various drugs. The microneedle devices can have a plurality of microneedles with a length of a few hundred microns. These devices are usually made from silicon or other metals using etching methods. Although effective, the resulting microneedle devices are expensive to manufacture and are difficult to produce in large numbers. One example of a microneedle device for delivering a drug to a patient is disclosed in U.S. Pat. No. 5,879,326 to Godshall et al.

Microneedle drug delivery devices are able to penetrate the stratum corneum of the skin with less irritation. The stratum corneum is a complex structure of compacted keratinized cell remnants having a thickness of about 10–30 microns and forms a waterproof membrane to protect the body from invasion by various substances and the outward migration of various compounds. The delivery of drugs through the skin is enhanced by either increasing the permeability of the skin or increasing the force or energy used to direct the drugs through the skin.

One method of delivering drugs through the skin is by forming micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al.; and WO 97/48440.

The prior methods and apparatus for the manufacture of micro-devices for medical use has exhibited some success but is generally time consuming and expensive. Accordingly, a continuing need exists in the industry for an improved method for the manufacture of micro-devices.

SUMMARY OF THE INVENTION

The present invention is directed to a method of manufacturing devices, such as, micro-devices for medical and other uses. The method and apparatus of the invention are suitable for molding plastic devices having micron and submicron features. The medical micro-devices are devices having channels, needles, points or other structural features having dimensions ranging from less than 1 micron to several hundred microns in length or width. Examples of micro-devices that can be molded in accordance with the present invention include analytical microchannel devices, microneedles, pipettes and the like. Analytical microchannel devices, for example, can include microchannels having a diameter ranging from about 0.5 microns to about 500 microns.

In one embodiment of the invention, the micro-device is used for penetrating or abrading the stratum corneum of the skin and for the transdermal delivery of a substance, such as a drug or pharmaceutical agent, through the abraded area. The device includes a plurality of microneedles for abrading and preparing a delivery site on the skin to enhance the delivery of a substance through the stratum corneum of the skin to a sufficient depth where the substance can be absorbed and utilized by the body.

Accordingly, a primary object of the invention is to provide a method for efficiently manufacturing a micro-device from plastic or other materials.

Another object of the invention is to provide a method of molding a micro-device from a polymeric material using a mold capable of molding submicron-size features which can be readily removed from the mold surface.

A further object of the invention is to provide a method of molding a micro-device from a polymeric material in a cost-efficient manner.

A further object of the invention is to provide a cost efficient method of manufacturing a device having microneedles of several microns in length.

Another object of the invention is to provide a method of molding a device having a plurality of microneedles having a length of about 5 to 250 microns.

A further object of the invention is to provide a method of manufacturing by injection molding a device having a plurality of microneedles with a needle density of about 4 to about 100 needles per $mm^2$.

A still further object of the invention is to provide a method of molding a micro-device having micron or submicron molded details without the use of a release agent on the mold surface.

Another object of the invention is to provide a mold assembly having a silicon molding surface for injection molding, compression molding or embossing to form a device having a plurality of molded micron or submicron features that can be easily removed from the mold without a release agent.

Still another object of the invention is to provide a method of molding a micro-device using a mold assembly having a mold cavity and silicon molding member attached to the mold assembly within the mold cavity.

The objects of the invention are further achieved by providing a method of molding a device having micron or submicron size features in a mold without the use of a release agent. The mold includes a mold member made of silicon or other material with suitable release properties and having a contoured surface defining an impression of the desired device for molding the micron or submicron size features from a polymeric material. The silicon mold member has a reverse image for molding the features where the molding surface can have recesses or peaks ranging from about 0.5 micron to several hundred microns in length.

The objects of the invention are substantially achieved by providing a method of making a device comprising providing a mold section with a recess defining a mold cavity where the mold cavity has a bottom wall and a silicon mold member disposed therein. The silicon mold member has a contoured surface facing the mold cavity. A hot polymeric material is introduced into the mold cavity to fill the mold cavity and the recesses in the silicon mold member to form a molded device. The mold assembly is then cooled and the molded device is removed from the mold cavity.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings, in which:

FIG. 6 is a top view of the silicon mold member used for molding a microneedle device.

DETAILED DESCRIPTION OF THE PREFERRED EMBODIMENT

Figure 1:
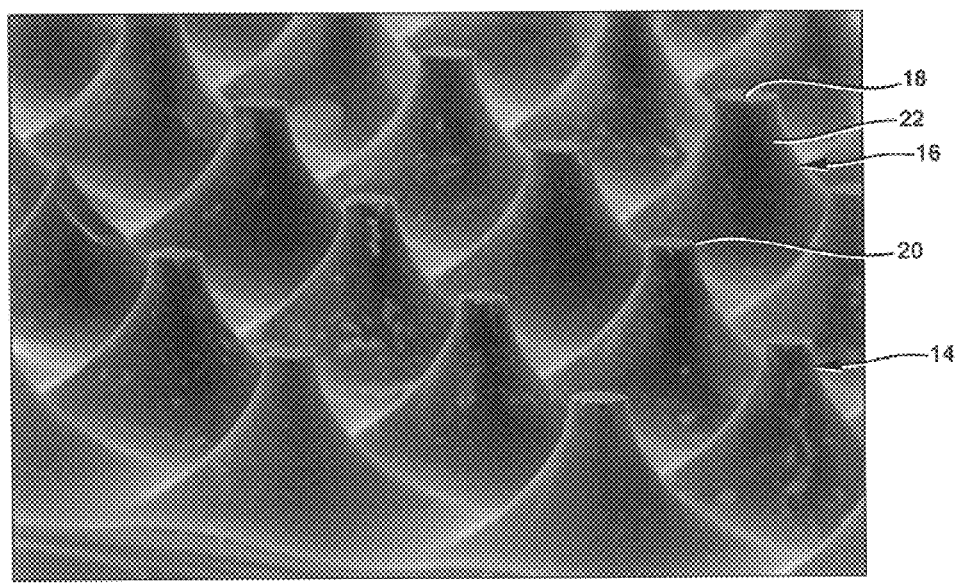
FIG. 1 is a perspective view of a microabrader surface one the embodiment of the invention.

The present invention is directed to a method of manufacturing a micro-device, such as a medical device, having a plurality of micron or submicron size features. In one embodiment the micro-device is a microabrader device for preparing the skin for transdermally administering a substance to a patient or withdrawing a substance from the body of a patient. The method of the invention is able to mold a device having a plurality of micron size features, such as a microabrader device, from a polymeric material. The molding method, such as injection molding, is able to produce a high volume of the devices with micron or submicron size features in an inexpensive manner and with a high degree of consistency.

The devices formed by the method of the invention are preferably devices that have micron or submicron size details integrally molded therein. Examples of micro-devices that can be molded by the method and apparatus of the invention include medical and analytical devices having micron size channels, conduits or capillaries, surgical needles, prosthetic devices, implants and the like. The method and molding apparatus are particularly suitable for the molded medical devices having channels, recesses, needles or other structural elements having at least one dimension ranging from about 0.5 micron to about 500 microns. The illustrated embodiment relates to a microneedle device for abrading the skin, although it will be understood that the invention is not limited to microabrader or microneedle devices and can be used to mold a variety of devices.

The microabrader devices made by the method of the present invention are particularly suitable for use in preparing skin for administering a pharmaceutical agent to a patient or withdrawing a substance transdermally from a patient. As used herein, a pharmaceutical agent includes a substance having biological activity such as antibiotics, antiviral agents, analgesics, anesthetics, anorexics, antiarthritics, antidepressants, antihistamines, anti-inflammatory agents, antineoplastic agents, vaccines (including DNA vaccines), and the like. Other substances which can be delivered intradermally to a patient include naturally occurring, synthesized or recombinantly produced proteins, peptides and fragments thereof. Substances and agents withdrawn from the body include analytes, drugs, glucose, body electrolytes, alcohol, blood gases, and the like.

In one embodiment of the invention, the method is directed to the manufacture of a microabrader for preparing the skin, and particularly the stratum corneum, for enhancing the delivery of a substance transdermally to a patient or for sampling various agents from the patient. The microabrader device is moved or rubbed on the skin to abrade and remove at least a portion of the stratum corneum. An active or passive drug delivery device or sampling device as known in the art is applied over the abraded area. As used herein, the term microabrader refers to a device which can abrade the skin to increase the permeability of the skin without causing unacceptable skin irritation or compromising the skin barrier to infectious agents.

In the illustrated embodiment shown in FIG. 1, the microabrader device 10 made by the method of the present invention includes a substantially planar body or support 12 having a plurality of microneedles 14 extending from the bottom surface of the support. The dimensions of the support 12 can vary depending on the length of the microneedles, the number of microneedles in a given area and the amount of the substance to be administered to the patient. Typically, the support 12 has a surface area of about 1–4 square centimeters ($cm^2$). In preferred embodiments, the support surface 12 has a surface area of about 1 $cm^2$.

Figure 2:
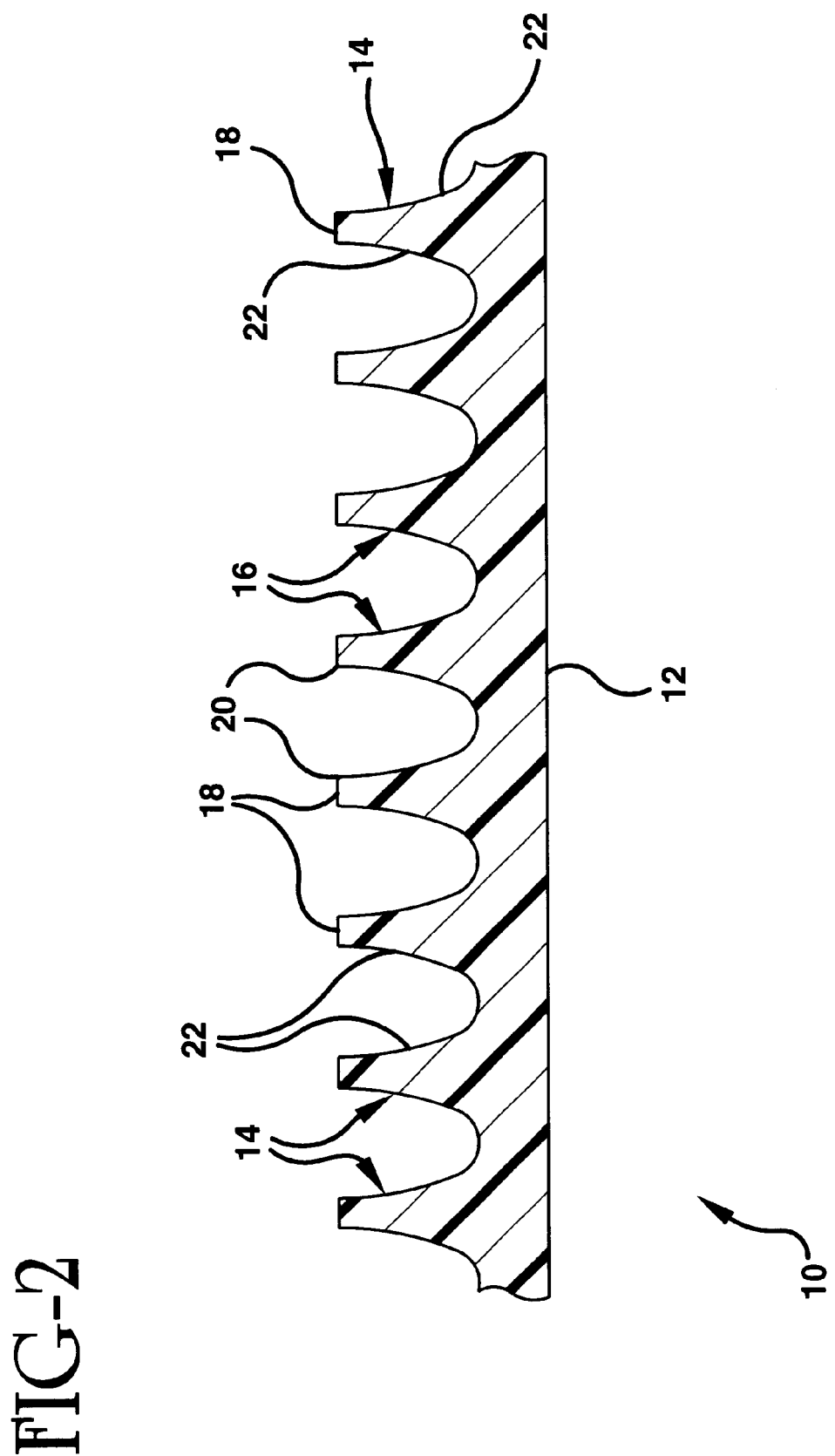
FIG. 2 is a partial cross-sectional view of the microabrader.
Figure 3:
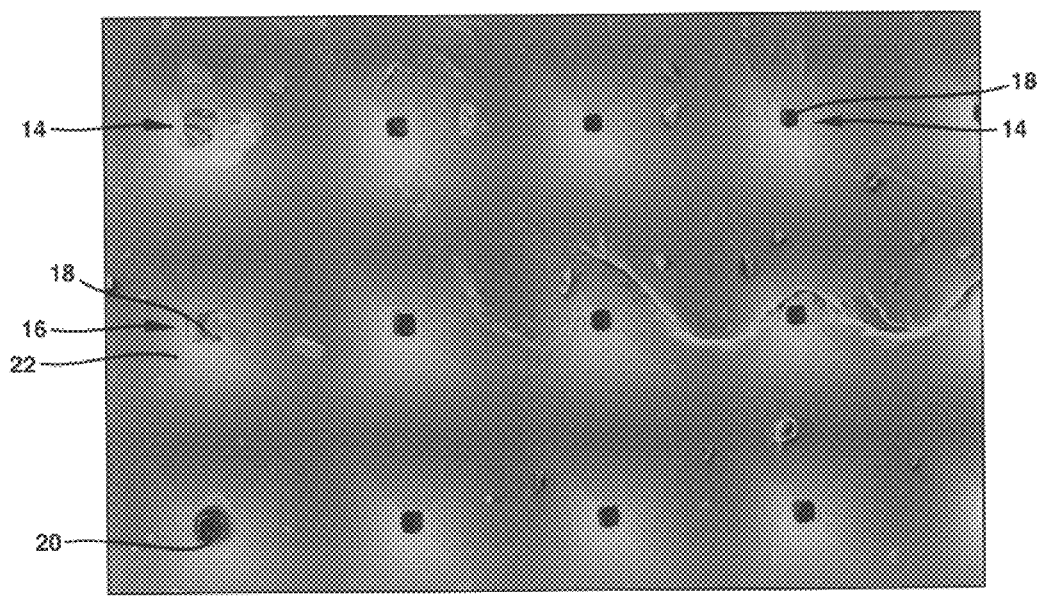
FIG. 3 is a top view of the microabrader in the embodiment of FIG. 1 showing the tips of the microneedles.

As shown in FIGS. 1 and 2, the microneedles 14 are integrally formed and attached to the surface of the support 12 and extend substantially perpendicular to the plane of the support 12. The microneedles 14 in the illustrated embodiment are arranged in a plurality of rows and columns and are substantially spaced apart a uniform distance. The microneedles 14 in this embodiment have a generally pyramidal shape with sides 16 extending to a tip 18. The sides 16 as shown have a generally concave surface when viewed in cross-section and form a curved surface extending from the support 12 to the tip 18. In the embodiment illustrated, the microneedles are formed by four sides 16 of substantially equal shape and dimension. As shown in FIGS. 2 and 3, each of the sides 16 of the microneedles 14 have opposite side edges contiguous with an adjacent side and form a scraping edge 22 extending outward from the support 12. The scraping edges 22 define a generally triangular or trapezoidal scraping surface corresponding to the shape of the side 16. In further embodiments, the microneedles 14 can be formed with fewer or more sides. Alternatively, the microneedles can be conical or cylindrical, with conical or pointed tips.

The microneedles 14 shown terminate at blunt tips 18. Generally, the tips 18 are substantially flat and parallel to the support 14. Each tip 18 preferably forms a well defined, sharp edge 20 where it meets the sides 16. The edge 20 extends substantially parallel to the support 12 and defines a scraping edge. In further embodiments, the edge 20 can be slightly rounded to form a smooth transition from the sides 16 to the tip 18.

The micro-devices, such as the microabrader device 10 and the microneedles 14 are made from a plastic material that is non-reactive with the substance being administered and that can be used in various molding processes, and particularly injection molding. Suitable plastic materials include, for example, polyethylene, polypropylene, polyamides, polystyrenes, polyesters and polycarbonates as known in the art. A preferred polymer is a high-flow polycarbonate available from GE Plastics under the trade name HF 1110.

The lengths and thicknesses of the microneedles are selected based on the particular substance being administered and the thickness of the stratum corneum in the location where the device is to be applied. The microneedles can have a length of about 5 microns up to about 250 microns. The microneedles in the illustrated embodiment have a generally pyramidal shape and are perpendicular to the plane of the device. The microneedles can be solid or hollow members.

As shown in FIG. 2 and 3, the microneedles 14 for microabrader are typically spaced apart uniformly in rows and columns to form an array. Typically, the rows of microneedles are spaced in rows to provide a density of about 2 to about 10 per millimeter (mm) and provide a needle density of about 4 to about 100 needles per $mm^2$, although the molding method of the invention enables the spacing to be varied as needed.

Figure 4:
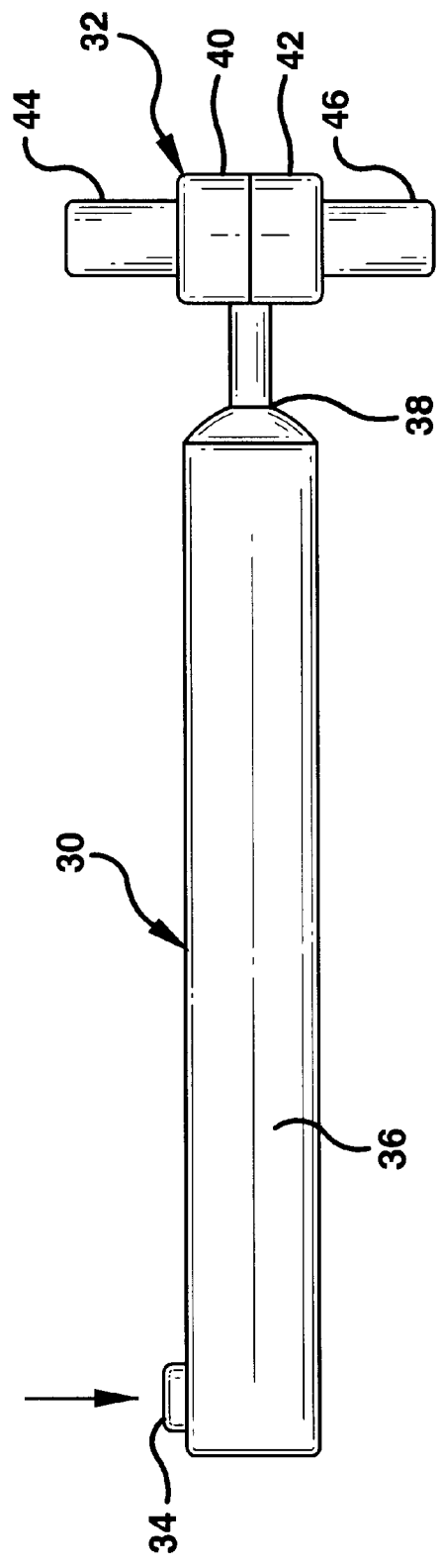
FIG. 4 is a schematic view of an injection molding apparatus used in one embodiment of the invention.

In a preferred embodiment, the micro-devices of the invention are manufactured by injection molding. Basically, the injection molding machine includes an extruder 30 and a mold assembly 32 as shown in FIG. 4. The extruder 30 is a commercially available extruder as known in the art for injection molding small parts. The extruder includes an inlet 34 for receiving the feed material which is generally in the form of pellets or flakes of the polymeric material. The pellets or flakes are conveyed through a barrel 36 where the pellets or flakes are heated to an extrudable temperature. The barrel 36 can be heated by electrical resistance heating or other methods as known in the extrusion art. A suitable injection molding machine can be, for example, an Arburg All Rounder 270S Universal.

The melted polymeric material is discharged from the extruder barrel through a discharge outlet 38 and supplied under pressure to the mold assembly 32. The mold assembly 32 is generally a two-piece mold having an upper mold section 40 and lower mold section 42. The upper mold section 40 and the lower mold section 42 are moved together and retracted during molding by control devices 44 and 46, respectively, to form and remove the molded device. The control devices 44 and 46 are generally operated by hydraulic or pneumatic piston and cylinder arrangements as known in the art. In the embodiment shown, the mold sections are shown as being vertically oriented. It will be apparent to one skilled in the art that the mold sections can be oriented horizontally or in another desired orientation without interfering with the molding process.

Figure 5:
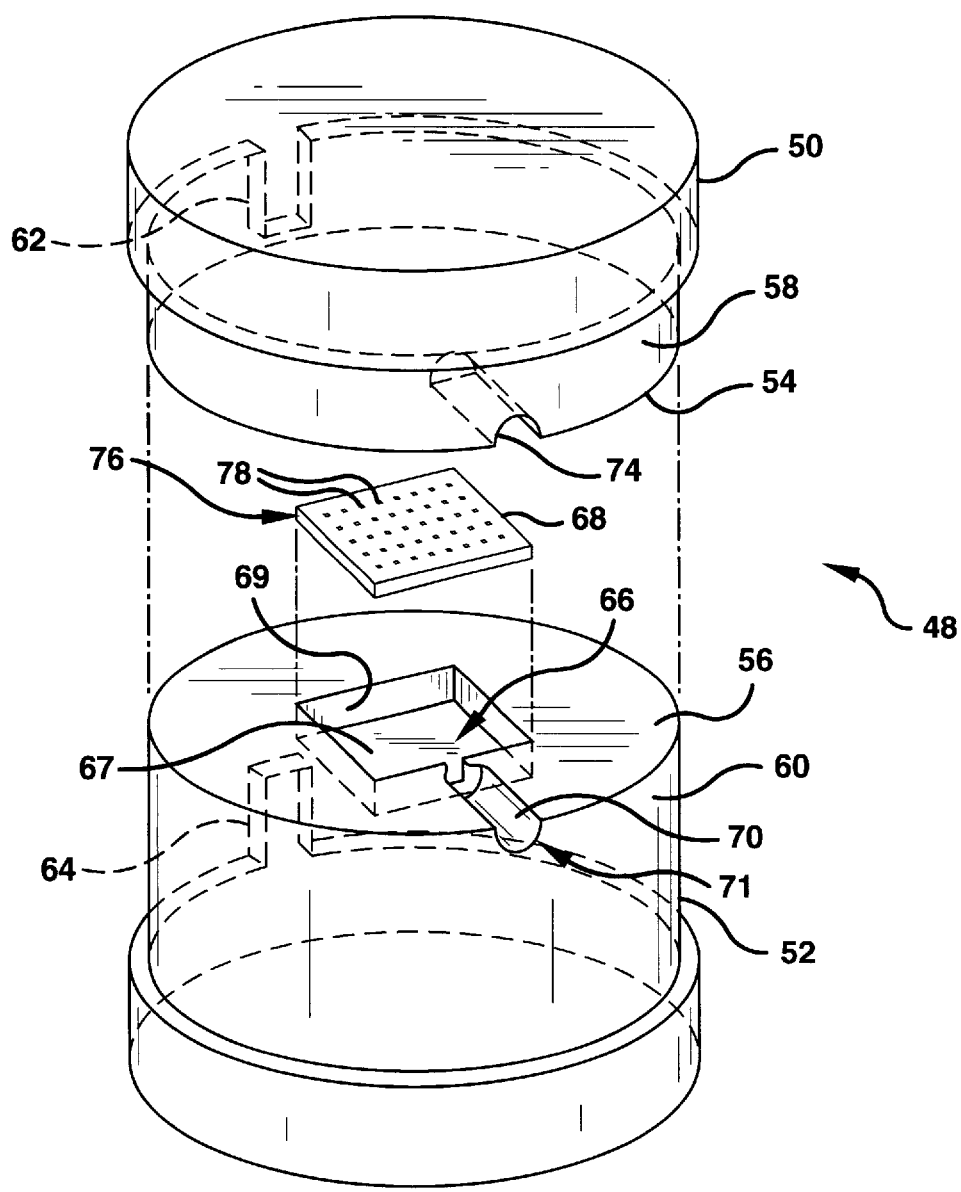
FIG. 5 is an exploded perspective view of a mold and silicon mold member for molding a microneedle device.

The mold assembly 32 includes a mold insert 48 as shown in FIG. 5 for molding the micro-device. The mold insert 48 can be made from a suitable material, which is typically a metal, such as steel, aluminum or other base metal. The mold insert 48 has a first section 50 and a second section 52 having mating surfaces 54 and 56, respectively. In the embodiment shown, the first section 50 and the second section 52 each have a generally cylindrical shape with an outer side wall 58 and 60. The mold insert sections are mounted in complementary recesses in the mold sections 40 and 42 as known in the art. Each mold insert section 50 and 52 has a key 62 and 64, respectively, on the outer side wall 58 and 60 for aligning the upper and lower mold halves during the molding process. The keys 62 and 64 slide in complementary grooves in the mold sections 40 and 42.

The mold section 52 includes a recess 66 which receives a mold member 68 and defines a mold cavity. The recess 66 is shown as being substantially square to correspond to the outer dimension of the resulting microneedle device. In further embodiments, the recess can be rectangular, circular or can have other desired shapes. The recess 66 has a depth corresponding to the thickness of the mold member 68 and the thickness of the molded micro-device. A semicircular supply recess 70 extends radially along the mating surface to the recess.

In preferred embodiments, the mold member 68 is made of silicon that is shaped to form the molded device. In further embodiments, other mold materials can be used that have suitable release properties. Examples of other mold materials that can be used including germanium, quartz, ceramics, glasses and materials having a low thermal expansion coefficient.

In the embodiment illustrated, the mold section 50 has a substantially flat surface 72 and a semicircular recess 74 extending radially inward from the side wall. The semicircular recess 74 is positioned to mate with the semicircular recess 70 of the mold insert section 52 to define a feed conduit 71 for supplying the polymeric material into the recess 66. In further embodiments, the surface 72 can have a suitable recess corresponding to the desired shape of the molded device.

The silicon mold member 68 is attached to the mold section 52 in the recess 66 by a suitable coupling device or a heat resistant adhesive, such as an epoxy adhesive. Typically, the silicon member 68 is adhesively attached to the face of the bottom wall 67 of the recess 66. In further embodiments, the silicon mold member 68 can be attached to the side wall 69 of the recess. The silicon mold member 68 has a generally square shape complementing the shape of the recess 66 and generally extends between the side walls 69 of the recess 66 in the embodiment illustrated. In further embodiments, the silicon mold member 68 can have a dimension less than the dimension of the bottom wall 67. An upper face of the silicon mold member 68 defines a mold surface 76 for forming and shaping the micro-device. The mold surface has a contoured surface in the form of an impression of the finished molded article. The mold surface can have at least one recess, ridge or peak having a width and/or height ranging from about 0.5 micron to about 500 microns depending on the device being molded. In the embodiment illustrated, the mold surface 76 of the silicon mold member has a plurality of recesses 78 as shown in FIG. 6 corresponding to the desired shape and dimensions of the microneedles for a microabrader device. When molding a microneedle device, the recesses can have a depth of about 5 to 250 microns and spaced to provide a density of about 4 to 100 recesses per $mm^2$. Accordingly, the mold surface 76 of the silicon mold member 68 is the reverse or impression of the molded micro-device. In one embodiment, the silicon mold member 68 has a thickness of about 0.020 inch.

In the illustrated embodiment, the mold surface 76 of the silicon mold member 68 can be shaped and formed using known techniques for shaping a silicon surface. Suitable methods include photolithography or wet etching as known in the art. Preferably, the recesses 78 in the silicon mold surface are formed by photolithography to form recesses 78 corresponding to the desired shape of the microneedles. Other shaping and forming techniques can be used to form the mold surface depending on the material of the mold surface.

The photolithography and wet etching methods are substantially the same as known by those skilled in the art for producing electronic components. Generally, the silicon mold member is made from a silicon wafer as used in the electronics industry. In further embodiments, the silicon mold member can be made using various micromachining processes which typically use a micron-size diamond milling machine. The micromachining processes are able to consistently reproduce silicon molding elements in various shapes and sizes that are not easily produced by photolithography.

The silicon mold member 68 functions as a mold surface for molding the device and provides significant advantages over other material surfaces for molding plastic devices, and particularly devices having micron and submicron details in a molded surface. The silicon mold member 68 provides complete release of the micro-device from the mold surface. The silicon molding surface effectively molds most polymeric materials with high resolution of the micron-size details and enables the molded device to be released from the mold without distorting or compromising the molded surface, and without the need for a release agent commonly used in many molding processes. Release agents applied to the mold surface can result in a loss of detail in the mold surface and resulting molded device. In addition, mold release agents which adhere to the molded device are considered to be contaminants for medical devices, which are required to be clean and sterile. In addition, the silicon mold member can be formed with micron-size details that are well defined and distinct and are able to transfer these details to the molded device.

The method of the invention is carried out by attaching the silicon mold member 68 with the surface formed in the desired shape in the recess 66 in the lower mold section 52 and assembling the upper and lower mold sections 50, 52 in the mold assembly 32. A polymeric material is supplied to the extruder 30 and heated to an extruding temperature. The mold halves 42, 44 are closed and the polymeric material injected through the feed conduit 71 of the mold sections into the recess 66 and against the silicon mold surface 76. The polymeric material and the mold are then cooled to harden the material. Thereafter, the mold sections 40, 42 are opened and the molded device is removed. The polymeric material is generally heated and processed according to the specifications recommended by the manufacturer. Since the silicon mold surface 76 enables injection molding of micron and submicron size details without the need for a release agent, which can contaminate the molded micro-device, the resulting molded device is substantially clean as it is ejected from the mold.

The molded device can also be made by other plastic molding processes. For example, a micro-device can be made by embossing a thermoplastic substrate with a silicon mold or platen. The silicon mold is provided with the impression of the desired molded micro-device. The device is formed by pressing the silicon mold under pressure against the plastic substrate that has been heated to its softening temperature. Alternatively, the silicon mold is heated and pressed against the thermoplastic substrate to mold the device.

In further embodiments, the device is formed by a compression molding method. In the compression molding method, a thermoplastic material, such as a powdered material, is placed in a hollow mold having a silicon molding surface. The mold is closed and the powdered thermoplastic is compressed under high pressure and heated to melt and consolidate the powder particles. The molded device is then removed from the mold.

In the embodiment illustrated, the mold surface 76 of the silicon mold member 68 is substantially flat. In further embodiments, the mold surface 76 can be curved, convex or concave over portions of the surface or over the entire surface. The mold surface can be non-planar to attain the desired shape of the molded device 10.

The molding processes can be carried out in a clean room as defined by clean room standards for particulate and pathogen contamination. For example, the molding can be in a work space at levels meeting or exceeding Class 100 as defined by Federal Standard No. 209E, "Airborne Particulate Cleanliness Classes in Clean Rooms and Clean Zones", approved by General Services Administration (Sep. 11, 1992). In further embodiments, the molded medical microdevice can be captured in a clean room or immediately packaged under clean room standards. Thereafter, the molded micro-device can be sterilized using standard sterilizing techniques such as gamma radiation or ethylene oxide gas when the packaging is permeable to the sterilizing gas.

While several embodiments have been shown to illustrate the present invention, it will be understood by those skilled in the art that various changes and modifications can be made therein without departing from the scope of the invention as defined in the appended claims.

What is claimed is:

1. A method of making a molded device comprising a plurality of micron or sub-micron size structural features, said method comprising the steps of:

providing a mold assembly having a mold section with a recess defining a mold cavity and having a silicon mold member disposed in said mold cavity, said silicon mold member having a mold surface with a contoured surface defining an impression of said device and said structural features facing said mold cavity;

introducing a plastic material into said mold cavity to fill said mold cavity and said contoured surface in said silicon mold member to form said molded device having a body and molded surface corresponding to said contoured surface and said structural features;

and removing said molded device from said mold section.

2. The method of claim 1, wherein said molded device has structural features which are a plurality of needles, about 5 to 250 microns in length.

3. The method of claim 2, wherein said needles are hollow.

4. The method of claim 1, wherein said silicon mold member releases said device from the mold surface and said molding is in the absence of a release agent, whereby said molded device is substantially clean and sterile.

5. The method of claim 1, wherein said mold cavity has a plurality of side walls and a bottom surface, and said silicon mold member is bonded to said bottom surface.

6. The method of claim 5, wherein said silicon mold member has an outer peripheral edge corresponding to the shape of said mold cavity, wherein said silicon mold member substantially covers said bottom surface of said mold cavity.

7. The method of claim 6, wherein said mold surface of said silicon mold member is substantially flat.

8. The method of claim 7, wherein said structural features comprise recesses which are provided in said mold surface and are spaced apart uniformly to form rows and columns, each of said recesses having a depth of about 5 to about 250 microns and said recesses being spaced to provide a density of about 4 to about 100 of said recesses per $mm^2$.

9. The method of claim 1, wherein said polymeric material is selected from the group consisting of polycarbonates, polyethylenes, polypropylene, polystyrene, polyesters and polyamides.

10. The method of claim 1, wherein said contoured surface of said silicon mold member has structural features comprising at least one recess, peak or ridge with at least one dimension ranging from about 0.5 micron to about 500 microns .

11. The method of claim 1, wherein said mold assembly includes an inlet in communication with said mold cavity, and said introducing step comprises injecting said plastic material through said inlet to said mold cavity.

12. The method of claim 1, wherein said introducing step comprises injecting a hot thermoplastic material into said mold cavity.

13. The method of claim 1, wherein said introducing step comprises introducing a thermoplastic material into said cavity and heating and compressing said thermoplastic material to mold said device.

14. The method of claim 1, wherein said introducing step comprises positioning a thermoplastic substrate on said mold cavity and pressing said mold assembly against said substrate to form said molded device.

15. A method of injection molding a device, said method comprising the steps of:

providing a mold assembly having a mold section with a recess defining a mold cavity, said recess having at least one side wall and a bottom wall, and a silicon mold member coupled to said mold section within said recess, said silicon mold member having a contoured mold surface facing said mold cavity and having at least one structural feature of about 5 to about 250 microns in at least one dimension;

closing said mold cavity and injecting a hot polymeric material into said mold cavity to substantially fill said mold cavity and to form a molded device, without said polymeric material adhering to said silicon mold member; and cooling the mold assembly and removing said molded device from said mold cavity, said molded device having a surface corresponding to said mold surface.

16. The method of claim 15, wherein said molded device is molded substantially in the absence of a release agent on said silicon mold member or said mold surface.

17. The method of claim 15, wherein said silicon mold member has an outer peripheral edge corresponding to the shape of said mold cavity, wherein said silicon mold member substantially covers said bottom wall of said mold cavity.

18. The method of claim 15, wherein said mold surface having at least one structural feature includes a plurality of spaced apart recesses forming rows and columns, said recesses being spaced to provide a density of about 4 to about 100 of said recesses per $mm^2$.

19. The method of claim 15, wherein said polymeric material is selected from the group consisting of polycarbonates, polyethylenes, polypropylene, polystyrene, polyesters and polyamides.

20. The method of claim 15, wherein said molded device is a microneedle device.

21. The method of claim 15, wherein said contoured surface of said silicon mold member and having at least one structural feature has as said structural feature at least one recess, peak or ridge with at least one dimension ranging from about 0.5 micron to about 500 microns.

22. The method of claim 1, wherein said structural features are selected from the group consisting of one or more channels, conduits, capillaries, needles, points, recesses and combinations thereof.

23. The method of claim 15, wherein said structural features are selected from the group consisting of one or more channels, conduits, capillaries, needles, points, recesses and combinations thereof.

24. The method of claim 7, wherein said mold surface having at least one structural feature includes a plurality of spaced apart recesses, said recesses being spaced to provide a density of about 4 to about 100 of said recesses per $mm^2$.

* * * * *